(12) United States Patent
Nibhanipudi

(10) Patent No.: US 11,135,458 B1
(45) Date of Patent: Oct. 5, 2021

(54) FACE MASK WITH MINI EXHAUST FAN

(71) Applicant: Kumara Venkatanarayana Nibhanipudi, Scarsdale, NY (US)

(72) Inventor: Kumara Venkatanarayana Nibhanipudi, Scarsdale, NY (US)

( * ) Notice: Subject to any disclaimer, the term of this patent is extended or adjusted under 35 U.S.C. 154(b) by 0 days.

(21) Appl. No.: 17/083,690

(22) Filed: Oct. 29, 2020

(51) Int. Cl.
*A62B 18/00* (2006.01)
*A62B 7/10* (2006.01)
*A61L 9/12* (2006.01)
*A61L 9/16* (2006.01)
*A61L 9/20* (2006.01)
*A62B 18/02* (2006.01)
*A62B 23/02* (2006.01)
*A62B 9/00* (2006.01)
*A62B 18/08* (2006.01)

(52) U.S. Cl.
CPC ............ *A62B 18/006* (2013.01); *A61L 9/122* (2013.01); *A61L 9/16* (2013.01); *A61L 9/20* (2013.01); *A62B 7/10* (2013.01); *A62B 9/00* (2013.01); *A62B 18/025* (2013.01); *A62B 18/08* (2013.01); *A62B 18/084* (2013.01); *A62B 23/02* (2013.01); *A61L 2209/212* (2013.01)

(58) Field of Classification Search
CPC ......... A62B 18/006; A62B 7/10; A61L 9/122; A61L 9/16
See application file for complete search history.

(56) References Cited

U.S. PATENT DOCUMENTS

| | | | |
|---|---|---|---|
| 6,698,427 B1 * | 3/2004 | Clowers | A61M 16/06 128/200.24 |
| 2015/0151147 A1 * | 6/2015 | Fun | A62B 18/025 128/206.17 |
| 2016/0001108 A1 * | 1/2016 | Zhou | A61L 9/00 128/863 |
| 2016/0016020 A1 * | 1/2016 | Sieber | B63C 11/24 128/205.12 |
| 2017/0128754 A1 * | 5/2017 | Hou | A62B 23/025 |
| 2018/0296864 A1 * | 10/2018 | Feasey | A62B 18/025 |

* cited by examiner

*Primary Examiner* — Kevin Joyner
(74) *Attorney, Agent, or Firm* — Blue Filament Law PLLC

(57) ABSTRACT

A mask is provided that includes a shell with an aperture. A fan assembly is positioned in the aperture and secured to the shell. The exhaust fan functions to dispel contaminants from the surface of the mask. A method of using the mask includes fitting the mask to the face and covering the nose and mouth and not the eyes. The mask is secured to the head. The fan is then activated to dispel contaminants from the surface of the mask.

15 Claims, 5 Drawing Sheets

(Section A-A)

FACE MASK WITH MINI EXHAUST FAN

FIELD OF THE INVENTION

The present invention in general relates to personal protective equipment and in particular to a face mask with an exhaust fan for dispelling contaminants from the surface of the mask.

BACKGROUND OF THE INVENTION

Motile or moving cilia are found throughout living organisms. Cilia have a rhythmic waving or beating motion. In the context of human respiratory function, cilia in the lungs and respiratory tract work to keep the airways clear of mucus and dirt, allowing a person to breathe easily and without irritation. For example, in the human nasal cavity, there are cilia which drive out the particulate material including viruses and bacteria.

However, some individuals experience a condition called primary ciliary dyskinesia (PCD) that is commonly referred to as immotile-cilia syndrome. PCD is characterized by congenital impairment of mucociliary clearance (MCC). The underlying cause is a defect of cilia in the airways, making the cilia unable to beat (ciliary immotility), unable to beat normally (ciliary dyskinesia), or absent altogether (ciliary aplasia). PCD is an inherited disease that has been described from most parts of the world and with equal prevalence in men and women of approximately one in 10,000 to 30,000 individuals. In patients with PCD, the patients have a decreased ability to drive out particulate and are prone to various infections, especially in the nasal cavity, where the cilia fail to drive out particulate material including viruses and bacteria.

Most common medical facemasks, illustratively including N93, N95, KN95, FFP2, P2, DS, nebulizer, or other face masks, as well as non-conventional face masks, have an inherent problem of organisms settling on the outer surface of any of these face masks and the organisms continuing to their respective dwellings in the patient.

Thus, there exists a need for improved personal protective equipment that mitigate the accumulation of organisms on their surfaces.

SUMMARY OF THE INVENTION

A mask is provided that includes a shell with an aperture. A fan assembly is positioned in the aperture and secured to the shell. The exhaust fan functions to dispel contaminants from the surface of the mask.

A method of using the mask includes fitting the mask to the face and covering the nose and mouth and not the eyes. The mask is secured to the head. The fan is then activated to dispel contaminants from the surface of the mask.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DESCRIPTION OF THE INVENTION

The present invention has utility as a facial personal protective equipment mask with an exhaust fan for dispelling contaminants from the surface of the mask. The usage of an inventive face mask containing a fan acts to drive out particulate matter before adhering to the face mask to and hence minimizes inhalation of bacteria and viruses by a wearer of an inventive face mask and and minimizes the patients inhaling of viruses and bacteria. It is appreciated that an inventive face mask is also well suited for patients with primary ciliary dyskinesia (PCD). The exhaust fan replaces the function of nasal cilia in PCD patients.

An inventive face mask also confers to the wearer an added benefit of not carrying the bacteria and viruses thereon and hence is particularly effective in preventing the community spread of infection to members of the same household and to social contacts.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Figure 1:
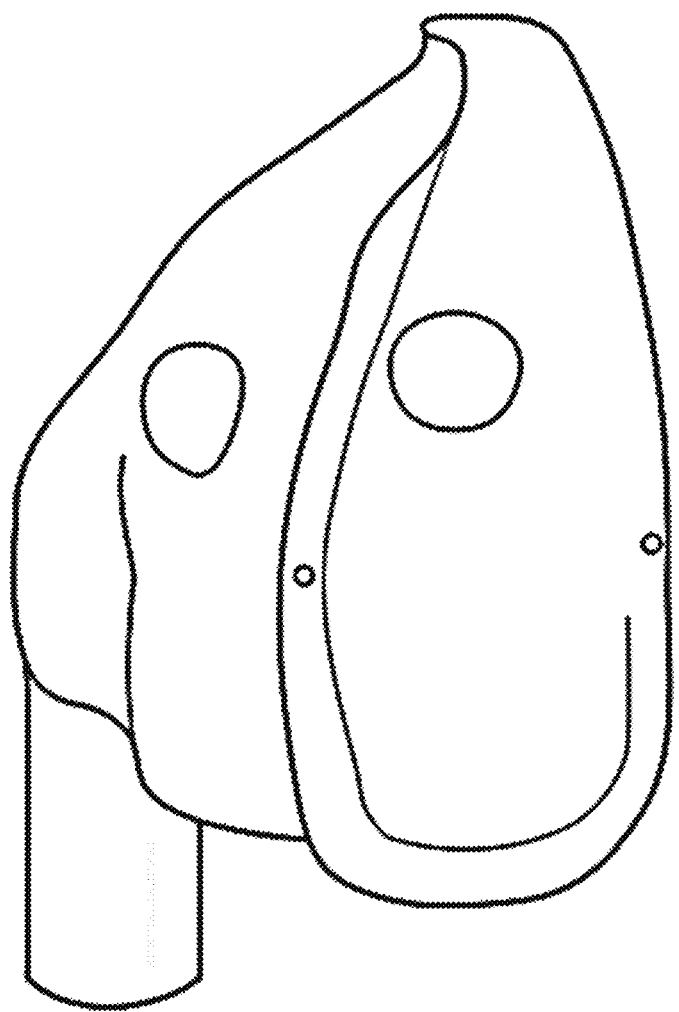
FIG. 1 is a perspective view of a conventional prior art nebulizer mask.

As used herein a facial personal protective equipment mask or respirator mask includes N93, N95, KN95, FFP2, P2, DS, nebulizer, or other face masks, as well as non-conventional face masks. A prior art nebulizer mask is shown in FIG. 1.

Figure 2:
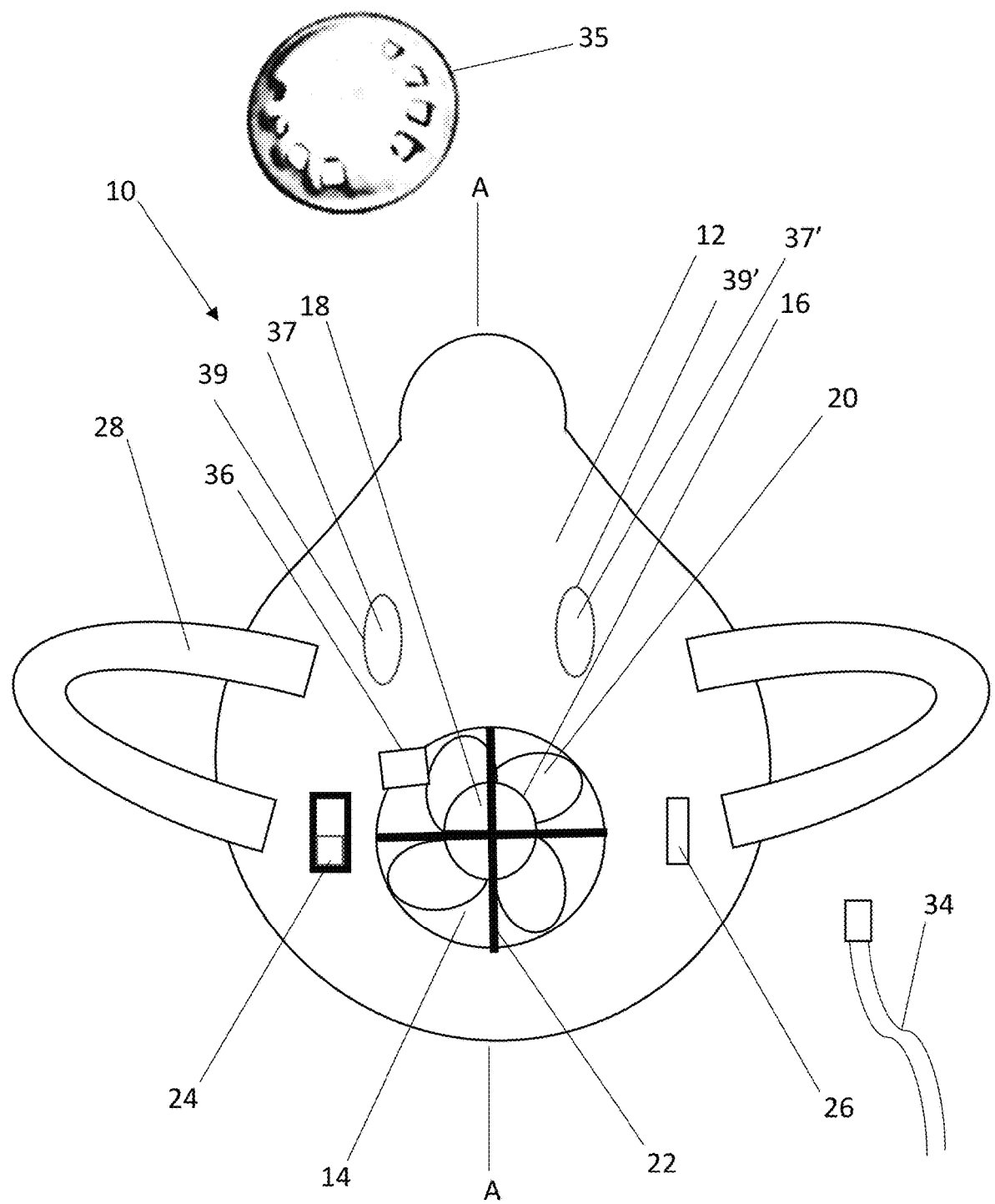
FIG. 2 illustrates a partially exploded frontal view of a facial mask equipped with a fan of in accordance with embodiments of the invention.
Figure 3:
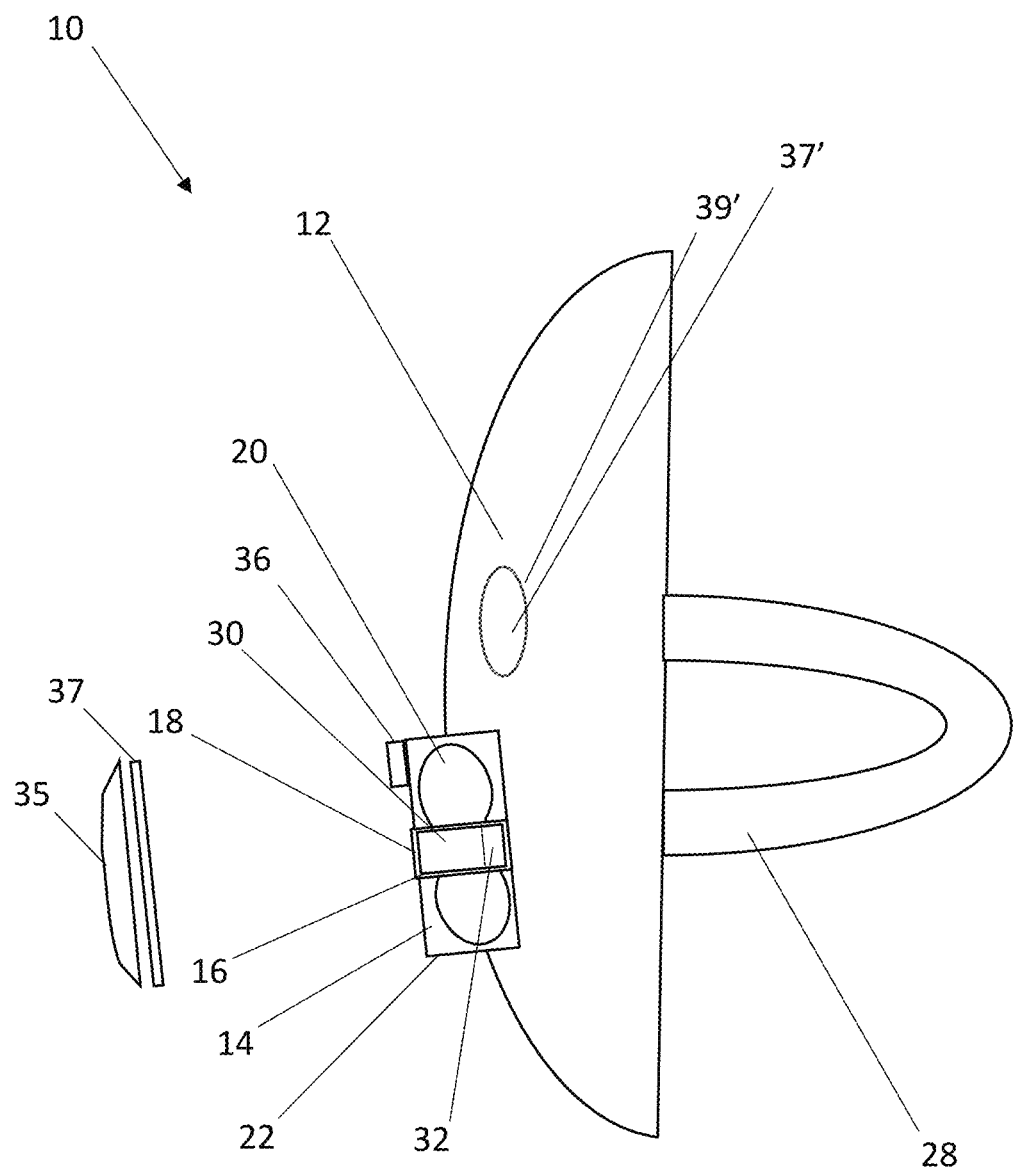
FIG. 3 is a partially exploded side cross sectional view along line A-A of FIG. 2.

With reference to the figures, FIG. 2 and FIG. 3 illustrate an embodiment of a facial mask 10 equipped with a fan 16. The shell 12 of the mask 10 is made of a one or more materials that maintain the shape of hemispherical or ovoid (oblong hemispherical) shapes that also supports an attached fan assembly 16. Materials that form the shell 12 illustratively include one or more of plastic, woven or spun fibers, and corrugated material. The fan assembly 16 fits in an aperture 14 formed in the shell 12. The fan assembly 16 includes a hub 18 with a set of blades 20 attached thereto. In inventive embodiments, the number of fan blades 20 varies between 2 and 6. It is appreciated that the number of fan blades may be more than six. The hub 18 houses a motor 30 powered by a power source 32. The motor 30 rotates the blades 20 in a direction that generally exhausts air away from the face of the wearer depending on the orientation of the blades 20. The power source 32 may be a single use battery or a rechargeable battery depending on whether the mask 10 is designed for single use or is a reusable mask. The fan assembly 16 is attached to the shell 12 by a cage 22 that attaches to the hub 18. A switch 24 controls the motion of the fan assembly 16. In inventive embodiments the fan maybe a single speed or an adjustable variable speed fan controlled by the switch 24. In the event of a rechargeable battery for the power source 32, a recharging port 26 is provided that connects to a removable charging cable 34. A set of fasteners 28 secure the mask 10 to the head of a user. It is appreciated that the set of fasteners 28 may be elastic straps that fit about the ears of the wearer, a set of tie strings, or hook and loop (Velcro®) straps. A removable cap 35 may fit over the cage 22 to protect a user from fan blade motion, while in other embodiments, seal the mask when required to protect the wearer from contagions. The removable cap 35 in some inventive embodiments includes a size exclusion filter 37 to preclude transmission of particles of a desired size range. To the extent that the mask 12 is a conventional mask per prior art FIG. 1, plugs 37, 37' cap the opposing holes 39, 39'.

In some inventive embodiments, a sterilizing device 36 is provided that functions to deactivate pathogens. A sterilizing device 36 operative herein illustratively includes an ultraviolet light emitting light emitting diode (LED), an electrostatic precipitator, an ozone generator, or combinations thereof.

As best shown in FIG. 3, in a specific inventive embodiment the fan assembly is positioned such that the blades 20 of the fan protrude both below and above the outer surface of the shell 12 in order to exhaust air away from the face of the user, as well as, to dispel particulate matter from the outer surface of the shell 12.

EXAMPLES

Example 1

A nebulizer mask was fitted with a fan having a circular base. The fan base contains a rechargeable battery driven motor that is attached to a set of fan blades. Half of the fan base body is positioned inside the lower portion of the face mask and the other half of the fan base body is outside the face mask, along with the attached set of fan blades. The fan has a switch to operate the fan. A charging port is provided for attachment of a charging cable for recharging battery. Once charged the battery lasts for 3 to 5 hours.

Example 2

Figure 4:
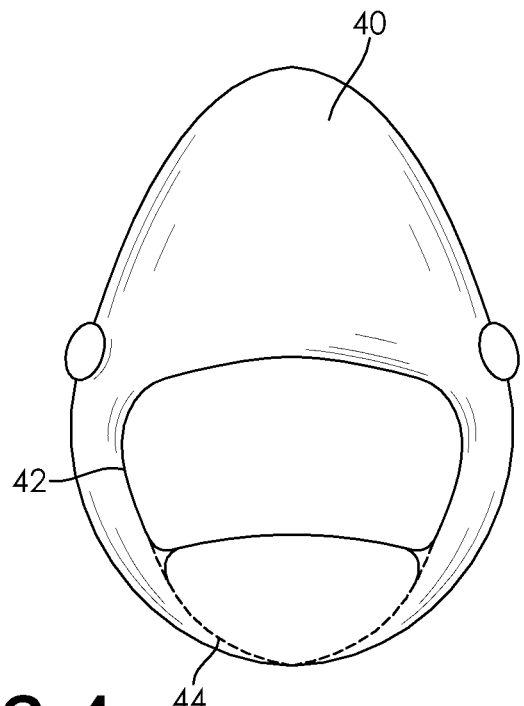
FIG. 4 is a frontal view of a facial mask with an aperture cut in the mask to accommodate a fan module in accordance with embodiments of the invention.
Figure 5:
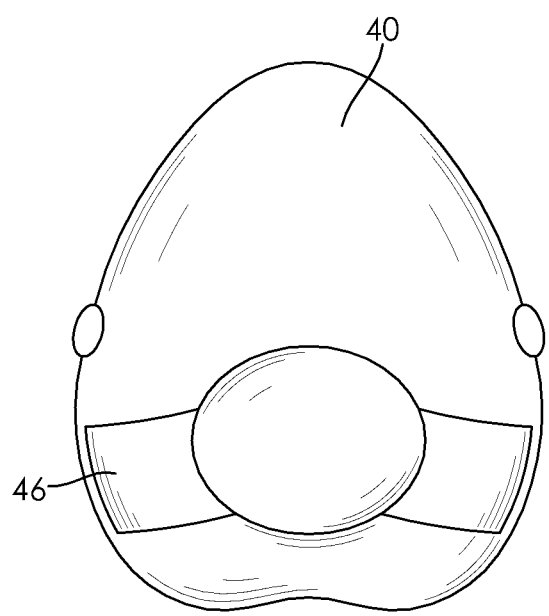
FIG. 5 is a frontal view of a modular fan support connected to the facial mask of FIG. 4.
Figure 6:
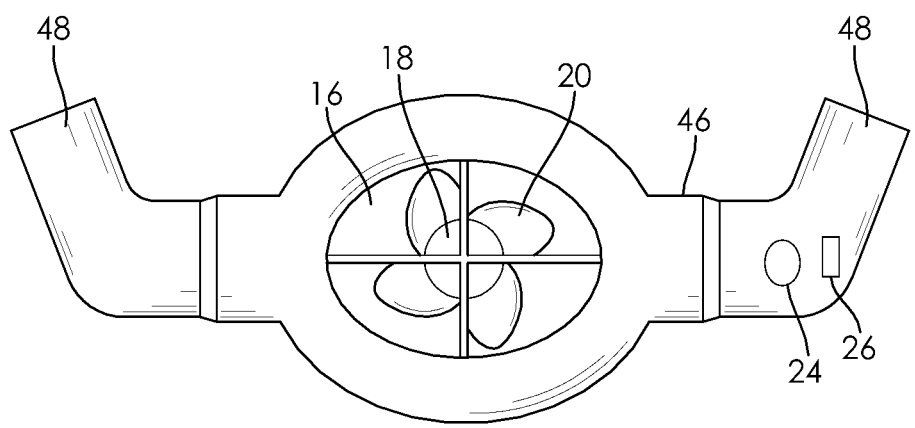
FIG. 6 is a detailed close up of the modular fan support of FIG. 5.

With reference to FIGS. 4 to 6, a wide aperture 42 was made through the external surface of a face mask 40 in the lower one third region of the mask 40 using a scalpel. In the embodiment shown, the aperture 42 measured horizontal 3 inches and vertical 2 and ¼th inches so that the base of the fan assembly 16 can be positioned in the lower inner portion of the face mask 40. In a specific embodiment the face mask 40 may be a nebulizer face mask in the manner shown in FIG. 1 that may be constructed of polyethylene. The bottom partially detached portion of the cut portion forms a flap 44 that may be used for additional support of the fan assembly 16 that is joined to a modular fan support 46. Half of the hub 18 of the fan assembly 16 is inside the lower face mask and the other half of the hub 18 is outside the face mask along with its attached fan blades 20. The modular fan support 46 has a switch 24 to operate the fan assembly 16 with a rechargeable battery and a recharging port 26 for attachment of a recharging cable 34 for recharging the battery. Securements 48 adhere the modular fan support 46 to the face mask 40. In specific inventive embodiments the modular fan support 46 is removably connected to the face mask 40 with securements 48.

Example 3

A method of using the mask of Examples 1 and 2 includes fitting the mask to the face and covering the nose and mouth and not the eyes. Securing the mask to the head, and activating the fan to exhaust air from the mask and dispel particulate matter illustratively including viruses and bacteria prior to adhering to the face mask.

The foregoing description is illustrative of particular embodiments of the invention but is not meant to be a limitation upon the practice thereof. The following claims, including all equivalents thereof, are intended to define the scope of the invention.

The invention claimed is:

1. A mask comprising:
a shell with an aperture, the aperture formed by cutting the shell and folding a resulting flap to form a support; and
a fan assembly including a cage to attach said fan assembly to said shell, said fan assembly further comprising a removable cap to fit over the cage to protect a user from a plurality of fan blades, said fan assembly positioned to rest on the flap and in the aperture and secured to said shell, said fan assembly set to exhaust air away from a face of a user wearing said mask and to dispel particulate matter from an outer surface of said shell;
a sterilizing device coupled to the shell, said sterilizing device comprising an ultraviolet light emitting diode, an electrostatic precipitator, or an ozone generator;
a switch located on said shell to control motion of the plurality of fan blades; and
a recharging port located on said shell, said recharging port connectable to a removable charging cable to recharge a power source for said fan assembly.

2. The mask of claim 1 wherein the shell is formed of one or more of plastic, woven or spun fibers, and corrugated material.

3. The mask of claim 1 wherein said fan assembly further comprises a hub that houses a motor and a power source.

4. The mask of claim 3 wherein said power source is a single use battery.

5. The mask of claim 3 wherein said power source is a rechargeable battery.

6. The mask of claim 5 further comprising a recharging port.

7. The mask of claim 3 wherein said hub is connected to said shell via a cage.

8. The mask of claim 1 further comprising a switch to control said fan.

9. The mask of claim 8 wherein said switch controls the speed of said fan.

10. The mask of claim 1 further comprising a set of fasteners to secure said mask to a user.

11. The mask of claim 1 wherein said fan assembly is positioned with a set of blades that protrude both below and above an outer surface of said shell.

12. The mask of claim 1 wherein said shell has a hemispherical or oblong hemispherical shape.

13. The mask of claim 1 further comprising a size exclusion filter adapted to be coupled to said removeable cap.

14. The mask of claim 1 wherein said cage holding said fan assembly supports a first half of a hub of said fan assembly inside said mask and a second half of the hub outside said mask along with the attached plurality of fan blades connected to said hub.

15. A method of using the mask of claim 1 comprises:
fitting the mask to the face and covering the nose and mouth and not the eye of a wearer;
securing the mask to a head of the wearer; and
activating said fan.

* * * * *